(12) United States Patent
Zhu et al.

(10) Patent No.: US 11,594,321 B2
(45) Date of Patent: Feb. 28, 2023

(54) RADIATION DOSE REDUCTION AND IMPROVED CONSISTENCY BETWEEN SESSIONS IN HYBRID IMAGING STUDIES

(71) Applicant: KONINKLIJKE PHILIPS N.V., Eindhoven (NL)

(72) Inventors: Yang-Ming Zhu, Solon, OH (US); Chi-Hua Tung, Aurora, OH (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 17/061,643

(22) Filed: Oct. 2, 2020

(65) Prior Publication Data
US 2021/0027881 A1 Jan. 28, 2021

Related U.S. Application Data

(63) Continuation of application No. 15/768,021, filed as application No. PCT/EP2016/076139 on Oct. 28, 2016, now Pat. No. 10,792,006.
(Continued)

(51) Int. Cl.
*G16H 30/20* (2018.01)
*A61B 6/03* (2006.01)
(Continued)

(52) U.S. Cl.
CPC ............. *G16H 30/20* (2018.01); *A61B 6/032* (2013.01); *A61B 6/037* (2013.01); *A61B 6/469* (2013.01);
(Continued)

(58) Field of Classification Search
CPC ......... A61B 6/542; A61B 6/032; A61B 6/037; A61B 6/469; A61B 6/5235; A61B 6/545; A61B 6/563; A61B 6/5205; A61B 6/4417
See application file for complete search history.

(56) References Cited

U.S. PATENT DOCUMENTS 7,209,579 B1 4/2007 Weisenberger
8,879,814 B2 11/2014 Wollenweber
(Continued)

FOREIGN PATENT DOCUMENTS

WO 00/10034 A1 2/2000

OTHER PUBLICATIONS

Rascovsky, et al., "Informatics in Radiology: Use of CouchDB for Document-based Storage of DICOM Objects", Radiographics., vol. 32, No. 3, May 1, 2012.
(Continued)

*Primary Examiner* — Hugh Maupin (57) ABSTRACT

In a multi-session imaging study, information from a previous imaging session is stored in a Binary Large Object (BLOB). Current emission imaging data are reconstructed into a non-attenuation corrected (NAC) current emission image. A spatial transform is generated aligning a previous NAC emission image from the BLOB to the current NAC emission image. A previous computed tomography (CT) image from the BLOB is warped using the spatial transform, and the current emission imaging data are reconstructed with attenuation correction using the warped CT image. Alternatively, low dose current emission imaging data and a current CT image are acquired, a spatial transform is generated aligning the previous CT image to the current CT image, a previous attenuation corrected (AC) emission image from the BLOB is warped using the spatial transform, and the current emission imaging data are reconstructed using the current CT image with the warped AC emission image as prior.

8 Claims, 5 Drawing Sheets

Related U.S. Application Data (60) Provisional application No. 62/248,443, filed on Oct. 30, 2015.

(51) Int. Cl.
*A61B 6/00* (2006.01)
*G16H 30/40* (2018.01)
*G16H 40/63* (2018.01)

(52) U.S. Cl.
CPC .......... *A61B 6/5235* (2013.01); *A61B 6/542* (2013.01); *A61B 6/545* (2013.01); *A61B 6/563* (2013.01); *G16H 30/40* (2018.01); *G16H 40/63* (2018.01); *A61B 6/4417* (2013.01); *A61B 6/5205* (2013.01)

(56) References Cited

U.S. PATENT DOCUMENTS

| | | |
|---|---|---|
| 2008/0310698 A1 | 12/2008 | Boeing |
| 2009/0110256 A1* | 4/2009 | Thielemans .............. G06T 7/30 382/131 |
| 2009/0276456 A1* | 11/2009 | Neubacher .......... G06F 16/2219 |
| 2010/0208037 A1* | 8/2010 | Sendai .................. A61B 6/462 348/46 |
| 2013/0004037 A1 | 1/2013 | Scheuering |
| 2014/0005519 A1 | 1/2014 | Kargar |
| 2016/0055658 A1 | 2/2016 | Liang |
| 2016/0089103 A1* | 3/2016 | Darrow .................. A61B 6/469 600/407 |

OTHER PUBLICATIONS

Ben-Cohen, et al., "Automated method for detection and segmentation of liver metastatic lesions in follow-up CT examinations" Journal of Medical Imaging, vol. 2, No. 3, Jul. 1, 2015.

Sotiras et al., "Deformable Medical Image RegisliaLion: A Survey", IEEE Trans. Med. Imaging vol. 32 No. 7 pages 1153 90 (2013).

Fayad, Hadi J. et al "Generation of 4-dimensional CT images based on 4-dimensional PET-derived motion fields", Journal of Nuclear medicine vol. 54 No. 4, (2013); pp. 631-638.

Lee, et al "Total radiation dose reduction in multiple session dynamic brain PET study using single CT scan", Journal of Nuclear Medicine, vol. 53, May 1, 2012, pp. 209.

* cited by examiner

RADIATION DOSE REDUCTION AND IMPROVED CONSISTENCY BETWEEN SESSIONS IN HYBRID IMAGING STUDIES

CROSS REFERENCE TO PRIOR APPLICATIONS

This application is a Continuation of U.S. application Ser. No. 15/768,021, filed Apr. 13, 2018, now U.S. Pat. No. 10,792,006, which is the U.S. National Phase application under 35 U.S.C. § 371 of International Application Serial No. PCT/EP2016/076139, filed on Oct. 28, 2016, which claims the benefit of U.S. Provisional Patent Application Ser. No. 62/248,443, filed on Oct. 30, 2015. These applications are hereby incorporated by reference herein.

FIELD

The following relates generally to the medical imaging arts, e.g. emission imaging such as positron emission tomography (PET) and single photon emission computed tomography (SPECT), computed tomography (CT), and combined emission/CT or other hybrid functional/anatomical imaging.

BACKGROUND

Emission imaging techniques such as positron emission tomography (PET) and single photon emission computed tomography (SPECT), on the one hand, and computed tomography (CT) imaging on the other hand, are complementary techniques. Emission imaging is performed by administering a radiopharmaceutical to a patient and imaging radiation emitted by the radiopharmaceutical tomographically using a ring of detectors or using detectors that revolve around the patient. Typically, the radiopharmaceutical is chosen to concentrate in a particular organ or tissue. For example, in oncological PET imaging the radiopharmaceutical is sometimes a sugar labeled with a positron-emitting radioisotope—as the cancerous tumor tends to take up sugar more rapidly than normal tissue, the tumor thus appears as a hot spot in the PET image. Emission imaging is therefore sometimes referred to as functional imaging as it can capture metabolic differences.

CT imaging measures transmission of x-rays through the patient. Tomographic imaging is usually obtained by revolving the x-ray source and detector array together around the patient, although configurations with ring-shaped x-ray sources and/or detector arrays are also known. CT contrast is due to differential x-ray absorption of different tissues, and accordingly CT generally provides anatomical, i.e. structural information. Thus, by acquiring both an emission image and a CT image, the cancerous tumor of the previous example can be located within the surrounding anatomy via the CT image and assessed as to its functional characteristics (e.g. extent of necrosis) via the emission image.

A further synergy of emission imaging and CT is that the CT image can be used to construct an attenuation map of the patient which is then used to correct for attenuation of the emission radiation when reconstructing the emission data. The CT image can be viewed as an attenuation map of the patient for radiation at the x-ray energy, and known scaling factors to account for the difference in x-ray energy (typically ~100-140 keV) and emission energies (e.g. 511 keV for PET) can be used to transform the CT image into a suitable attenuation map for the emission data reconstruction. For notational convenience, an emission image reconstructed without such attenuation correction is referred to herein as a non-attenuation corrected emission image or NAC-emission image (e.g. a NAC-PET image in the case of PET imaging). Similarly, an emission image reconstructed with attenuation correction using an attenuation map for the emission energy generated from a corresponding CT image is referred to herein as an attenuation corrected emission image or AC-emission image (e.g. a AC-PET image in the case of PET imaging).

In view of these synergies between emission imaging and CT imaging, it is common to perform a combined PET/CT or SPECT/CT imaging session in which both emission data (PET or SPECT data) and CT data are collected. The extensive use of this imaging combination is reflected in the commercial availability of combined PET/CT and SPECT/CT imaging systems, such as the Vereos PET/CT and BrightView SPECT/CT imaging systems, both available from Koninklijke Philips N.V., Eindhoven, the Netherlands. In combined emission/CT imaging, the CT data are reconstructed to form a CT image which is further transformed into an attenuation map for use in the PET or SPECT data reconstruction, thereby yielding both a CT image and an AC-PET or AC-SPECT image. Medical personnel commonly consider both the CT and AC-emission images as complementary information in performing medical assessments.

SUMMARY

In one disclosed aspect, an imaging controller comprising an electronic processor is programmed to perform an imaging method executing a current imaging session which is part of a multi-session imaging study of a subject. The imaging method includes: retrieving imaging data acquisition and reconstruction parameters of a previous imaging session of the imaging study from a Binary Large OBject (BLOB) that stores information for the imaging study including at least the imaging data acquisition and reconstruction parameters of the previous imaging session. An imaging system is automatically configured with the retrieved imaging data acquisition and reconstruction parameters of the previous imaging session. After the automatic configuring, the imaging system is controlled to acquire current imaging data from the subject and to reconstruct the current imaging data to generate a current image of the subject. The imaging data acquisition and reconstruction parameters used in the controlling are stored in the BLOB as the imaging data acquisition and reconstruction parameters of the current imaging session of the imaging study.

In another disclosed aspect, an imaging controller comprising an electronic processor is programmed to perform a reduced radiation dose imaging method including: acquiring current emission imaging data from a subject using an emission imaging system; reconstructing the current emission imaging data without attenuation correction to generate a non-attenuation corrected current emission image of the subject; generating a spatial transform to spatially align a previous non attenuation corrected emission image to the current non attenuation corrected emission image of the subject; warping a previous computed tomography (CT) image that is spatially aligned with the previous non-attenuation corrected emission image using the spatial transform to generate a warped CT image; and reconstructing the current emission imaging data with attenuation correction performed using the warped CT image to generate an attenuation-corrected current emission image of the subject.

In another disclosed aspect, an imaging controller comprising an electronic processor is programmed to perform a reduced radiation dose imaging method including: acquiring current emission imaging data from a subject using an emission imaging system; acquiring a current CT image of the subject using a CT imaging system; generating a spatial transform to spatially align a previous CT image to the current CT image of the subject; warping a previous attenuation corrected emission image that is spatially aligned with the previous CT image using the spatial transform to generate a warped attenuation corrected emission image; and reconstructing the current emission imaging data with attenuation correction performed using the current CT image and using the warped attenuation corrected emission image as prior data to generate an attenuation-corrected current emission image of the subject.

One advantage resides in performing combined emission (e.g. PET or SPECT) and CT imaging with reduced radiation dosage to the patient.

Another advantage resides in providing faster combined emission/CT imaging.

Another advantage resides in providing a workflow for assessing whether such foregoing advantage(s) can be achieved without undue loss of image quality or reliability in a given imaging session.

Another advantage resides in providing quantitative assessment of whether a past CT image can be re-used.

Another advantage resides in providing improved consistency between successive imaging sessions of a multi-session emission/CT imaging study.

A given embodiment may provide none, one, two, more, or all of the foregoing advantages, and/or may provide other advantages as will become apparent to one of ordinary skill in the art upon reading and understanding the present disclosure.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention.

DETAILED DESCRIPTION

One problem recognized herein is that existing medical imaging architectures do not comport with modern imaging tasks such as oncology treatment protocol monitoring. For example, fractionated radiation therapy treatment protocols deliver radiation over a series of successive radiation therapy sessions. Similarly, chemotherapy is often performed in successive sessions. In between these sessions, various tests are scheduled, including typically two or more (sometimes several successive) PET/CT or SPECT/CT imaging sessions, in order to assess the progress of the treatment. These imaging sessions provide the oncologist with radiological feedback as to whether the therapy sessions are having the desired effect and necrotizing the cancerous tumor.

However, to be effective the successive PET/CT or SPECT/CT imaging sessions should be "comparable" in that differences in images acquired from one imaging session to the next should be attributable to changes in the subject (e.g. tumor shrinkage or growth, tumor angiogenesis or necrosis, or so forth), and should not be due to differences in the particulars of the imaging sessions themselves. With existing imaging system architectures, however, it is common to have successive imaging sessions performed by different radiologists, different imaging settings, different image reconstruction settings, and/or different post-acquisition processing. Any or all of these differences can result in observable difference in images from successive imaging sessions, which however are not attributable to changes in the imaging subject but rather to the different image settings, reconstruction settings, or so forth.

Embodiments disclosed herein address this problem by providing a treatment protocol-level control using a treatment protocol Binary Large Object (BLOB) data structure for collecting and storing information (or pointers to information) related to a single treatment protocol (e.g. a fractionated radiation therapy protocol for an oncology patient).

Another problem recognized herein with existing emission/CT imaging systems and workflows is that the patient is subjected to a high dose of radiation to due to receiving radiation dosage from both from the radiopharmaceutical administered for the emission imaging and from x-ray transmission through the patient during the CT imaging. The radiation dosage concern is further enhanced in therapy regiments that employ successive emission/CT imaging sessions over time to monitor the patient, such as is the case in many fractionated radiation therapy, brachytherapy, or chemotherapy cancer treatment regimens as discussed further below.

Improved emission/CT imaging systems and workflows disclosed herein leverage past CT images, or in some embodiments past emission images, of the patient to reduce radiation exposure. Such past images are often available in treatment protocols that call for performing two or more (sometimes several successive) PET/CT or SPECT/CT imaging sessions in order to assess the progress of the treatment. For example, in a fractionated radiation therapy protocol, therapeutic radiation is administered over a series of successive radiation therapy sessions, and PET/CT imaging sessions are usually scheduled at designated times between radiation therapy sessions.

It is further recognized herein that, over the course of such a therapy protocol, the patient's general anatomy as observed by the CT is less likely to change dramatically as compared with the functional behavior of the tumor as observed by the PET imaging. Therefore, it is advantageous to re-use a past CT image for a current imaging session if it can be demonstrated that the past CT image is still representative of the patient's anatomy. Techniques disclosed herein provide quantitative assessment of whether the past CT image can be re-used, and disclose effective approaches for re-using the past CT image when the quantitative assessment indicates that such re-use is appropriate.

In some emission/CT imaging tasks, the principle source of radiation dosage to the patient is from the radiopharmaceutical used in the emission imaging. In these instances, it would be preferable to reduce the radiopharmaceutical dosage used in the emission imaging rather than reducing x-ray exposure. In such cases, embodiments disclosed herein provide effective ways to leverage a past emission image in order to employ a reduced radiopharmaceutical dosage in the current emission imaging session.

Figure 1:
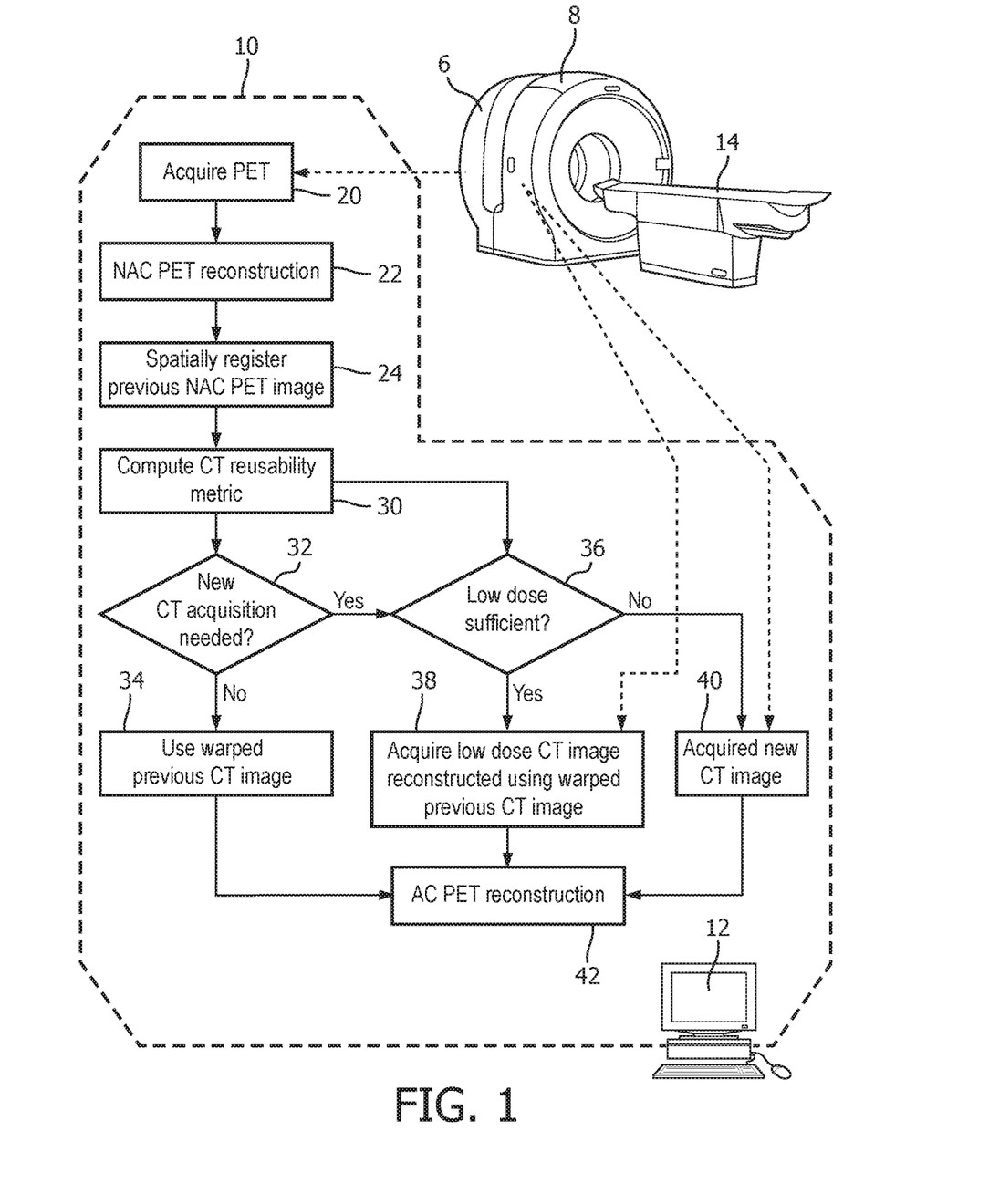
FIG. 1 diagrammatically illustrates a PET/CT imaging system including a system controller programmed to implement an imaging workflow including assessment of whether radiation exposure of the patient can be reduced by re-using a past CT image.

With reference to FIG. 1, a combined emission/computed tomography (CT) imaging system includes an emission imaging system, such as an illustrative positron emission tomography (PET) imaging system 6, or a single photon emission computed tomography (SPECT) system (not shown), and a computed tomography (CT) imaging system 8. The combined imaging system further includes an imaging controller 10 comprising an electronic processor 12 configured to acquire and process emission imaging data from a subject (e.g. an oncology out-patient or in-patient, a cardiac out-patient or in-patient, or so forth) using the emission imaging system 6, and configured to acquire and process CT imaging data of the subject using the CT imaging system 8. Such image processing may include "cross-modality" operations involving both emission and CT images, such as reconstructing an emission image with attenuation correction performed using a CT image.

The imaging controller 10 is diagrammatically illustrated in FIG. 1, and is implemented by a suitably programmed electronic processor 12 such as an illustrative computer 12, or a dedicated imaging controller server, or so forth. Disclosed image or imaging data acquisition operations performed by the imaging controller 10 using one of the imaging systems 6, 8 are understood to entail the imaging controller 10 sending appropriate control signals to the imaging system via suitable operative control connections (not shown). Typically, the imaging systems 6, 8 also include on-board or associated electronics which may be viewed as components of the electronic processor 12 embodying the imaging controller 10. For example, these on-board or associated electronics may handle low-level operations such as operating the x-ray tube and controlling gantry rotation, while a separate computer or other electronic device may interface with the radiologist and send high-level instructions to the on-board imaging electronics. Further, the electronic processor 12 may be partially implemented as a server accessed via a hospital network. For example, the electronic processor 12 may comprise on-board electronics for lower-level functions, a desktop computer programmed with imaging system control software enabling a radiological technician to select and run an imaging sequence that is executed by the on-board electronics and imaging system hardware, and a server-based image processing program that performs data processing tasks such as image reconstruction, spatial registration of images, scaling of CT images to generate attenuation maps at the emission imaging energy, and so forth.

In a combined emission/CT imaging session, the emission images acquired by the emission imaging system 6 and the CT images acquired by the CT imaging system 8 are spatially aligned or share a common spatial geometry so as to facilitate comparisons by the radiologist and to facilitate use of a CT image as an attenuation map for attenuation-corrected emission imaging data reconstruction. In a combined emission/CT system such as the combined imaging system 6, 8 of FIG. 1, this is facilitated by using a common subject support 14 for loading the patient into either imaging system 6, 8.

Additionally or alternatively, the spatial alignment or shared common spatial geometry can be achieved in whole or in part by way of post-acquisition image processing, that is, by spatially registering the emission image and CT image using intrinsic location markers (discrete anatomical features) and/or externally attached location markers that are visible in both the emission and CT images. In this approach, a spatial transform is computed to spatially align one image to another image. The spatial transform is then applied to the one image to warp the one image into spatial alignment with the other image. Depending upon the amount and type of misalignment (rigid or non-rigid), numerous spatial alignment or spatial registration algorithms are known which can be used for generating the spatial transform. Some examples of deformable image registration algorithms are described, by way of non-limiting example, in Sotiras et al., "Deformable Medical Image Registration: A Survey", IEEE Trans. Med. Imaging vol. 32 no. 7 pages 1153-90 (2013).

Figure 2:
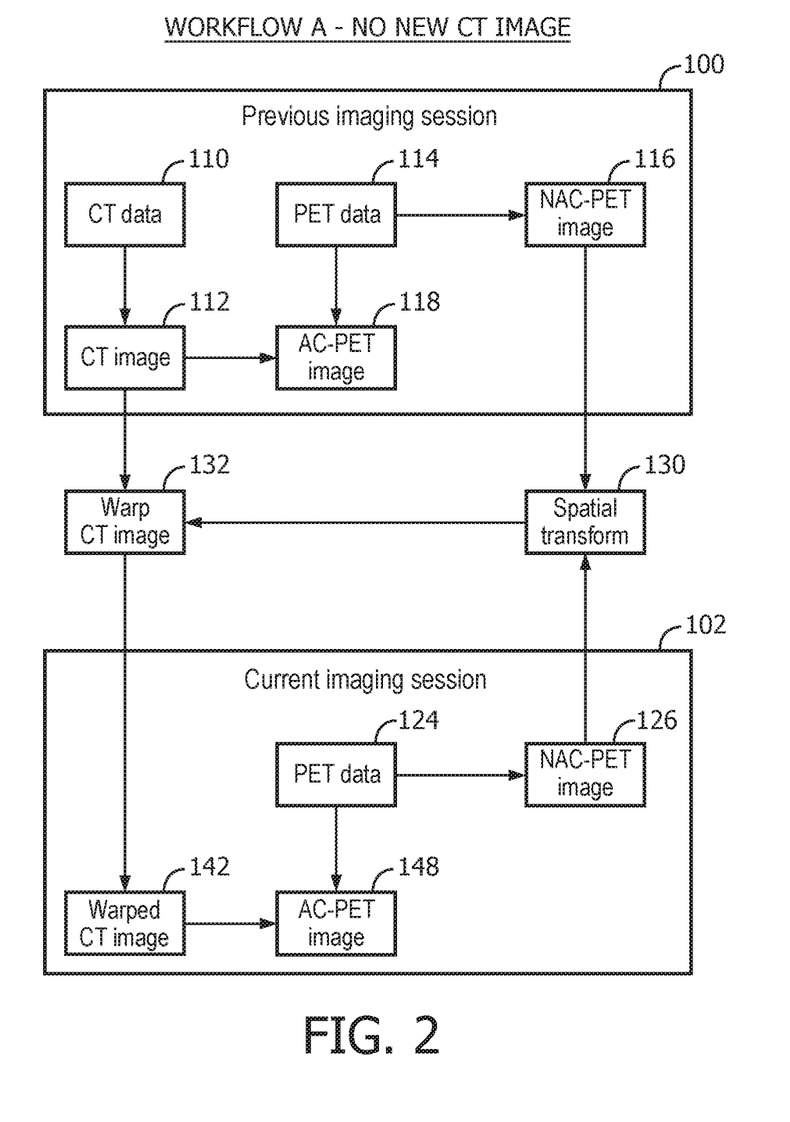
FIG. 2 diagrammatically shows a Workflow A suitably performed by the system of FIG. 1 when the assessment is that no new CT image is needed.
Figure 3:
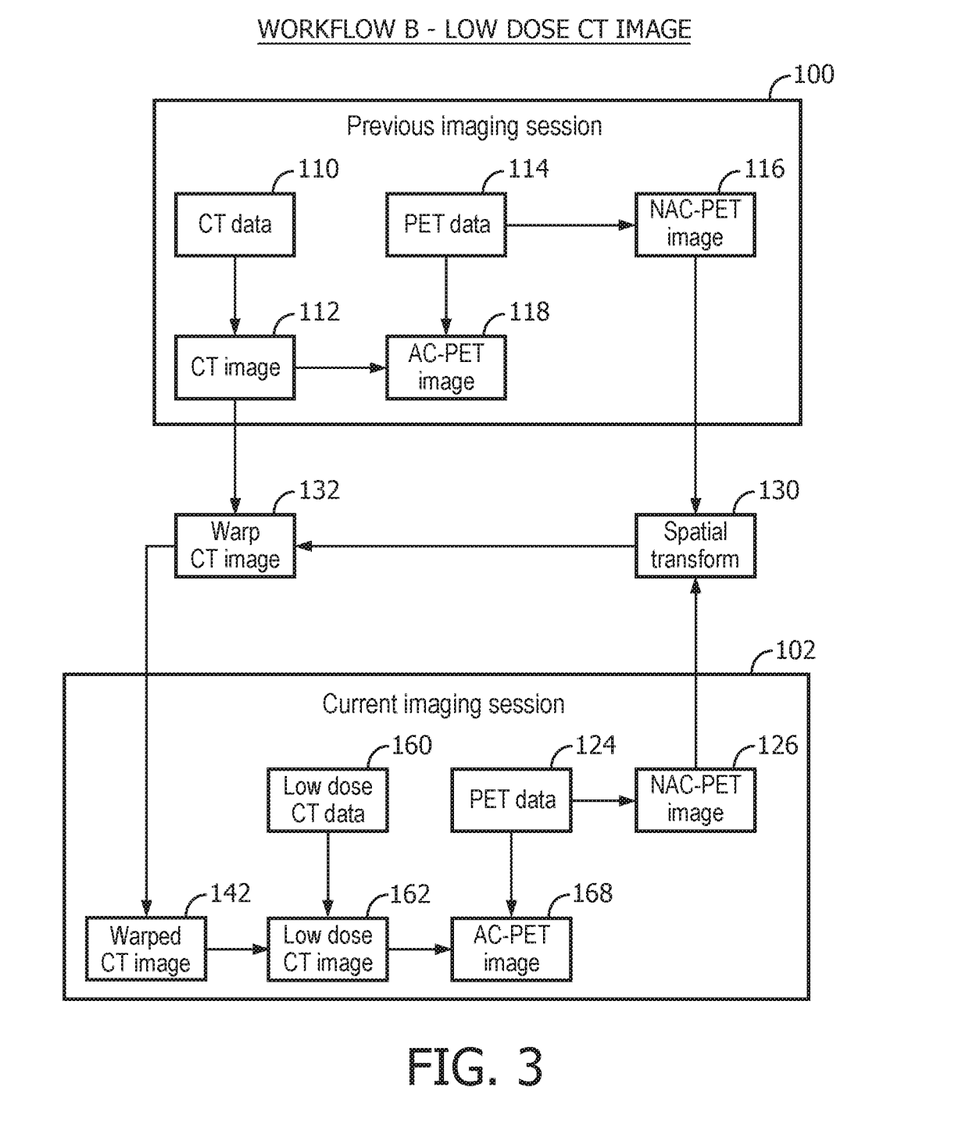
FIG. 3 diagrammatically shows a Workflow B suitably performed by the system of FIG. 1 when the assessment is that a new low dose CT image is sufficient.

Before continuing with the description of the system of FIG. 1, two illustrative reduced radiation dose imaging methods disclosed herein are described with reference to FIGS. 2 and 3, respectively. In the method of FIG. 2, referred to herein as "Workflow A", a previous CT image, for example from a previous emission/CT imaging session, is leveraged to avoid acquiring a new CT image in a current imaging session. In the method of FIG. 3, referred to herein as "Workflow B", the previous CT image is again leveraged, but to improve the reconstruction of a low dose CT image acquired in a current imaging session. That is, Workflow B enables reduced x-ray dosage to the patient by leveraging the previous CT image to allow for using lower x-ray dose in the current imaging session, the reduced CT imaging data quality due to the lower x-ray dose being offset by additional information provided by the previous CT image. For clarity of explanation, Workflow A and Workflow B are described in the context of PET imaging being the emission imaging modality, but it will be appreciated that the techniques can be similarly implemented for other emission imaging modalities such as SPECT.

Turning first to Workflow A of FIG. 2, it is assumed that there is a previous PET/CT imaging session 100, whose images (or at least the imaging data from which images can be reconstructed) are available at the time a current PET/CT imaging session 102 is performed, for example stored in a Picture Archiving and Communication System (PACS). The previous imaging session 100 acquired CT imaging data 110 which was reconstructed to generate a CT image 112, and acquired PET imaging data 114 which was reconstructed without performing attenuation correction to produce a non-attenuation corrected (NAC) PET image 116. Although the illustrative embodiments employ PET imaging, alternatively the image 116 could be a SPECT image or other type of emission image; even more generally, the disclosed techniques may be applied to multimodality hybrid imaging studies generally such as hybrid PET/magnetic resonance (MR) or SPECT/MR imaging studies (e.g., with PET or SPECT providing functional information and MR providing anatomical information). Typically, the previous imaging session 100 will also have reconstructed an attenuation-corrected (AC) PET image 118 which was reconstructed with attenuation correction performed using the CT image 112 of the previous session 100. This AC-PET image 118 is not used in the processing of the current imaging session 102 disclosed herein, but is typically available since attenuation correction substantially improves the diagnostic value of the PET image, and accordingly the radiologist who performed the radiology reading of the previous imaging session 100 will likely have wanted to read the AC-PET image 118 rather than the NAC-PET image 116. Indeed, since the NAC-PET image 116 is usually not desired for the radiology reading, in some cases the NAC-PET image 116 may not be available in the PACS—but it can be readily reconstructed from the PET data 114 which is stored in the PACS when needed for the current imaging session 102.

Turning to the current imaging session 102, this session usually occurs a substantial time after the previous imaging session 100, e.g. at least one day after in most cases, and commonly a few days to a few weeks later for a typical oncology treatment workflow. The time interval between the successive imaging sessions 100, 102 is long enough that some therapy has usually been delivered in the interim, e.g. one or more chemotherapy and/or radiation therapy sessions of a fractionated oncology therapy regimen, and the objective of the current imaging session 102 is to assess the impact of the therapy, e.g. hopefully to observe some shrinkage and/or necrosis of the tumor in the case of effective oncology treatment; or to observe continued growth/viability of the tumor which would indicate the oncology therapy has not yet been effective. Typically the radiopharmaceutical for the PET imaging is administered to the patient, e.g. intravenously, prior to the start of imaging data acquisition. In some common PET imaging workflows, the radiopharmaceutical is administered a few tens of minutes to a half-hour or so before the start of PET imaging data acquisition, the time being dictated by the requisite time for the radiopharmaceutical to accumulate in the tumor or other organ or tissue of interest. The patient is loaded into the imaging system, and PET imaging data 124 for the current imaging session 102 are acquired. In Workflow A, these PET imaging data 124 are initially reconstructed, without attenuation correction, to generate a NAC-PET image 126 for the current imaging session 102.

The goal in Workflow A of FIG. 2 is to avoid the need to acquire a new CT image by instead re-using the CT image 112 of the previous imaging session 100 for attenuation correction of the PET data and to serve as the anatomic image for the radiology reading. However, it is generally expected that the spatial geometry will have shifted to some degree between the previous imaging session 100 and the current imaging session 102. This geometry shift may be caused by a different positioning of the patient on the subject support 14 for the current imaging session 102 as compared with the previous imaging session 100. The geometry shift may also be due to changes in the physiology of the patient between the two imaging sessions 100, 102, due to factors such as differences in bladder fluid levels, shifting of internal organs, or weight gain or loss. It is recognized herein that the latter, i.e. weight change, is the most common source of significant non-rigid change in the spatial geometry between successive imaging sessions. This is especially true in the case of patients undergoing chemotherapy and/or radiation therapy, for whom significant weight loss is a common side-effect. By contrast, bladder levels are usually similar since there is usually a common preparatory sequence including withholding fluids for a fixed time period before the imaging session, and any geometry change due to different positioning is readily accommodated by the image registration process.

With continuing reference to FIG. 2, the existence of NAC-PET images 116, 126 for both the previous and current imaging sessions 100, 102 is leveraged to determine a spatial transform 130 to spatially align the previous NAC-PET image 116 to the current NAC-PET image 126 of the subject. The spatial transform 130 is determined by performing a deformable spatial image registration to register the previous NAC-PET image 116 to the current NAC-PET image 126 of the subject. Various non-rigid spatial image registration techniques can be used, such as by way of non-limiting example one of those described in Sotiras et al., "Deformable Medical Image Registration: A Survey", IEEE Trans. Med. Imaging vol. 32 no. 7 pages 1153-90 (2013). This approach can be used with either conventional PET imaging data or time-of-flight (TOF) localized PET imaging data; typically TOF-PET imaging data will provide more accuracy for the spatial transform 130 since the TOF localization provides improved spatial resolution. In an operation 132, the previous CT image 132 (which again is spatially aligned with the previous NAC-PET image 116) is warped using the spatial transform 130 to generate a warped CT image 142. The PET imaging data 124 of the current imaging session 102 are then reconstructed with attenuation correction performed using the warped CT image 142 as an attenuation map to generate an AC-PET image 148 of the subject for the current imaging session 102.

As previously noted, when a CT image is used as an attenuation map in performing attenuation corrected emission imaging data reconstruction, it is typical to apply known scaling factors to account for the difference in x-ray energy (typically ~100-140 keV) and emission energies (e.g. 511 keV for PET). This scaling corrects for different absorption coefficients for the x-rays as compared with the 511 keV gamma rays, and merely adjusts the intensity values of the CT image. Accordingly, the scaling can be performed at any point in the processing. For example, in Workflow A of FIG. 2 the previous CT image 112 can be scaled before the warping 132 to adjust for the difference between particle energy of the emission data and particle energy of the x-rays; alternatively, the scaling can be performed on the warped CT image 142 after performing the warping 132 but before its use in reconstructing the current PET imaging data 124 with attenuation correction to generate the AC-PET image 148.

With continuing reference to FIG. 2, the images of the current imaging session 102 which are read by the radiologist include the AC-PET image 148 and the warped CT image 142, the latter of which is relied upon for anatomic information. Preferably, the warped CT image 142 is labeled appropriately, e.g. with an acquisition date and perhaps with information on the applied spatial transform 130, so that the radiologist performing the reading is made aware that this image was acquired in an earlier imaging session. It will be appreciated that the approach of Workflow A described with reference to FIG. 2 is most appropriately used in situations in which the patient anatomy at the time of the previous imaging session 100 as characterized by the previous CT image 112 is fairly similar to the patient's current anatomy at the time of the current imaging session 102. For more significant anatomy changes, the assumption that the warped CT image 142 adequately represents the patient anatomy at the time of the current imaging session 102 becomes less appropriate.

With reference to FIG. 3, a modified reduced radiation dosage imaging method, called Workflow B herein, is described. Workflow B is suitably employed when the patient anatomy has changed significantly between the previous and current imaging sessions 100, 102 such that the spatial transform 130 alone is insufficient to reliably re-use the previous CT image 112. Workflow B of FIG. 3 is the same as Workflow A of FIG. 2 up to the point where the warped CT image 142 is generated. However, in Workflow B the warped CT image 142 is not directly used as the anatomic image for the current imaging session 102. Rather, in Workflow B the current imaging session 102 further includes acquiring low dose CT imaging data 160 with an x-ray dose that is lower than the x-ray dose that was used to acquire the previous CT image 112 of the previous imaging session 100. In some implementations, the low dose CT acquisition used to acquire the low-dose CT imaging data 160 uses only about one-fourth to one-fifth or less of the radiation dose of a regular CT acquisition (such as that used to acquire the previous CT image 112). The low dose acquisition may be obtained by operating the x-ray tube at lower continuous power, and/or by employing shuttering of the x-ray tube at intervals (e.g. to employ limited projection and/or fewer angular sampling, sometimes called sparse view CT). In either case, the resulting CT imaging data 160 inherently has lower signal-to-noise ratio (SNR) as compared with regular CT imaging data such as the CT imaging data 110 of the previous imaging session 100. To compensate for this lower SNR data 160, the warped CT image 142 from the previous imaging session 100 warped using the spatial transform 130 is used as prior information in reconstructing the low dose CT imaging data 160 to generate a low-dose CT image 162. For example, the warped CT image 142 may be used as an a priori during the CT image reconstruction, using an algorithm such as total variance minimization based projection onto convex sets. The PET imaging data 124 of the current imaging session 102 are then reconstructed with attenuation correction performed using the low dose CT image 162 as an attenuation map to generate an AC-PET image 168 for the current imaging session 102.

With reference returning back now to FIG. 1, a control process is described by which the imaging controller 10 implements either Workflow A (FIG. 2) or Workflow B (FIG. 3), or acquires a new full-dose CT image for the current imaging session, using a CT reusability metric to decide between these options. Referring now to FIG. 1, in an operation 20 PET imaging data are acquired using the PET imaging system 6. These data correspond to the PET imaging data 124 of the current imaging session 102 of FIGS. 2 and 3. In an operation 22, the PET imaging data are reconstructed, without attenuation correction, to produce the NAC-PET image 126 of the current imaging session 102 of FIGS. 2 and 3. In an operation 24, the previous NAC-PET image 116 is spatially registered with the current NAC-PET image 126 to produce the spatial transform 130 of FIGS. 2 and 3.

In an operation 30, a CT reusability metric is computed, which quantitatively assesses how well the warped CT image 142 would represent the anatomy of the patient at the time of the current imaging session 102 of FIGS. 2 and 3. In some illustrative embodiments, the CT reusability metric is based on at least one of (1) weight change of the subject between a time of acquisition of the previous NAC-PET image 116 (i.e. the time of acquisition of the PET imaging data 114 of the previous imaging session 100) and a time of acquisition of the current emission imaging data 124 and (2) a relative overlap metric between the current NAC-PET image 126 of the subject and the previous NAC-PET image 116 spatially aligned using the spatial transformation 130.

If weight change is a factor in the CT reusability metric, then the CT reusability metric is preferably constructed such that a smaller weight change of the subject favors Workflow A of FIG. 2 over Workflow B of FIG. 3, and favors Workflow B over the approach of acquiring a new full-dose CT image in the current imaging session 102. This reflects the expectation that a smaller weight change favors reasonableness of re-using the previous CT image 112.

Relative overlap can be calculated, for example, by segmenting both the current NAC-PET image 126 and the previous NAC-PET image 116 after applying the spatial transform 130 and calculating the ratio of the common volume and superset of volumes. Relative overlap can be viewed as a metric of how well the spatial transform 130 operates to match the previous NAC-PET image 116 to the current NAC-PET image 126. If relative overlap is a factor in the CT reusability metric, then the CT reusability metric is preferably constructed such that a higher relative overlap metric (i.e. greater overlap) favors Workflow A of FIG. 2 over Workflow B of FIG. 3, and favors Workflow B over the approach of acquiring a new full-dose CT image in the current imaging session 102. This reflects that a higher overlap indicates the spatial transform 130 is more effective at matching the geometry of the previous imaging session 100 to the geometry of the current imaging session 102, thus favoring reasonableness of re-using the previous CT image 112.

At a decision block 32, it is determined whether a new CT image is needed. If the decision is that a new CT image is not needed, then in an operation 34 the warped CT image 142 is used as the attenuation map. This corresponds to Workflow A of FIG. 2. Decision 32 can, for example, decide to pass to operation 34 (Workflow A) if the patient weight change is less than a threshold percentage or relative overlap is greater than a threshold percentage. Again, it is contemplated to use only one of these factors (e.g. only weight change, or only relative overlap). Conversely, if there are multiple factors, a weighted sum or a voting scheme or the like can combine the factors to make the decision 32.

If at the decision block 32 it is determined that a new CT image is needed, then flow passes to a second decision block 36 where it is determined whether a low-dose CT image is sufficient or whether a full-dose CT image is needed. If it is determined that a low-dose CT image is sufficient then process flow passes to a block 38 which follows Workflow B (FIG. 3), i.e. low-dose CT imaging data 160 are acquired using the CT imaging system 8 and these data are reconstructed using the warped previous CT image 142 as prior information to generate the low-dose CT image 162 which serves as the attenuation map. On the other hand, if it is determined that a new full-dose CT image is needed then in an operation 40 the CT imaging system 8 is used to acquire a full-dose CT image which is reconstructed without using the previous CT image 112 in any way. (The "full-dose" CT image is acquired using the usual dose for a PET/CT study. This "full dose" is still typically lower than the dose used in some other tasks such as diagnostic CT). Decision 36 can, for example, decide to pass to operation 38 (Workflow B) if the patient weight change is less than a threshold percentage (which is larger than the threshold percentage used in decision 32) or relative overlap is greater than a threshold percentage (which is smaller than the threshold percentage used in decision 32). Otherwise, flow passes to operation 40 which does not re-use the previous CT image 112 at all.

With continuing reference to FIG. 1, in an operation 42 the current PET imaging data 124 of FIGS. 2 and 3 are reconstructed using the chosen attenuation map (i.e., the warped previous CT image 142 if flow passes through operation 34/Workflow A, or the low-dose CT image 162 if flow passes through operation 38/Workflow B, or the newly acquired full-dose CT image if flow passes through operation 40).

In some embodiments, the thresholds used in the decision operations 32, 36 may be user-selectable or set for a particular application (e.g. may be different depending upon the anatomic region being imaged, e.g. lung versus heart versus brain or so forth).

The previous imaging session 100 is preferably a previous imaging session of the same subject as in the current imaging session 102 (i.e., same individual and same anatomic location/orientation). This increases the reasonableness of expecting the warped CT image 142 to be a good representation of the current anatomic state of the subject. However, it is alternatively contemplated for the previous CT and PET images to be of another individual, although it should still be of the same anatomic location in the same orientation, and the CT and PET images of the previous session should still be mutually spatially aligned. For example, it is contemplated for the previous imaging session 100 (i.e. the previous NAC-PET 116 and the previous CT image 112) to be PET/CT study atlas images retrieved from an electronic PET/CT study atlas.

The examples of FIGS. 1-3 achieved reduced dose to the patient by eliminating acquisition of a current CT image entirely (Workflow A of FIG. 2) or by enabling use of a low-dose current CT image (Workflow B of FIG. 3). In other embodiments, it is contemplated to achieve reduced dose imaging by reducing the dosage of radiopharmaceutical employed during the emission imaging.

Figure 4:
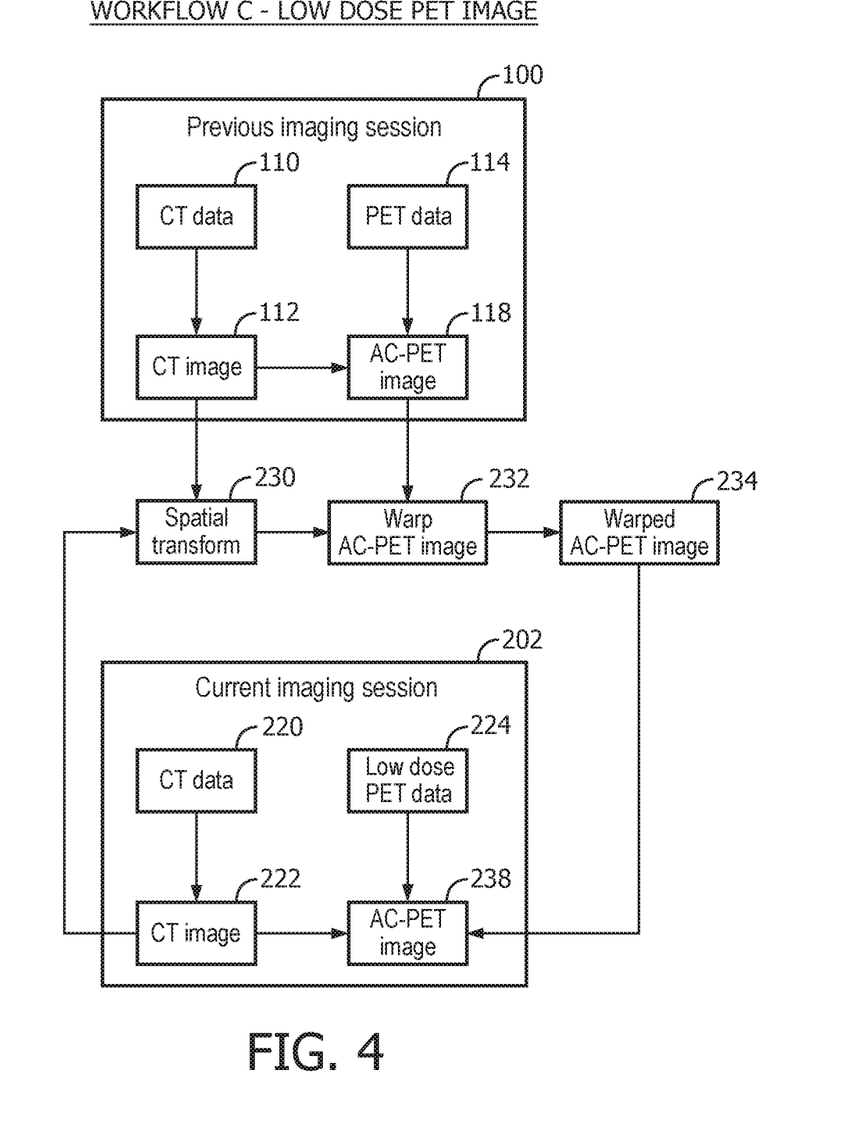
FIG. 4 diagrammatically shows a Workflow C suitably performed by the system of FIG. 1 in which the CT imaging is performed conventionally but the PET image is acquired using a reduced radiopharmaceutical dosage.

With reference to FIG. 4, an example of this is described, again using PET as the illustrative emission imaging modality. Since the emission imaging captures functional features, which are expected to change more rapidly over time as compared with anatomical features, an approach analogous to Workflow A (FIG. 2) is not appropriate. Rather, the Workflow C of FIG. 4 is more closely analogous to Workflow B, as Workflow C similarly uses low-dose imaging facilitated by re-use of the previous imaging session. The method of Workflow C (FIG. 4) again relies upon the previous imaging session 100 including the previous CT image 112 and the previous AC-PET image 118. (In Workflow C the non-attenuation corrected emission image, i.e. NAC-PET image 116 of FIGS. 2 and 3, is not used). In Workflow C, the goal is to reduce dosage on the emission imaging side: accordingly, CT data 220 are collected in a current imaging session 202 performed after the previous imaging session 100, and are reconstructed to generate a current CT image 222. The CT image 222 is typically a full-dose image, although a reduced-dose CT image as in the image acquisition 160, 162 of Workflow B of FIG. 3, is also contemplated. Low-dose PET imaging data 224 are also acquired in the current imaging session 202. "Low dose" PET imaging data means the PET imaging data are acquired with a dose of radiopharmaceutical that is lower than the dose of radiopharmaceutical used to acquire the "full dose" PET imaging data 114 of the previous imaging session. (However, Workflow C would also work if the PET imaging data acquired in the current imaging session 202 were full-dose PET imaging data). A spatial transform 230 is generated in the same way as the spatial transform 130 of Workflows A and B of respective FIGS. 2 and 3, except that the spatial transform 230 is generated to spatially align the previous CT image 112 to the current CT image 222 of the subject. Again, various non-rigid spatial image registration techniques can be used, such as by way of non-limiting example one of those described in Sotiras et al., "Deformable Medical Image Registration: A Survey", IEEE Trans. Med. Imaging vol. 32 no. 7 pages 1153-90 (2013). In an operation 232, the previous AC-PET image 118 (which again is spatially aligned with the previous CT image 112 which was used in the attenuation correction of the AC-PET image 118) is warped using the spatial transform 230 to generate a warped AC-PET image 234. The low-dose PET imaging data 224 of the current imaging session 202 are then reconstructed with attenuation correction performed using the current CT image 222 as an attenuation map and using the warped AC-PET image 234 as prior data to generate an AC-PET image 238 of the subject for the current imaging session 202. In one approach, the warped previous PET priori 234 is modeled and considered explicitly as in the sparse view CT reconstruction algorithm. Just as a good priori reduces the CT dose required for CT reconstruction, a good priori AC-PET also reduces the dose requirement (i.e. radiopharmaceutical dose) for PET acquisition and reconstruction. The decent estimate provided by the warped previous PET priori 234 can also be used as initial image for iterative AC-PET reconstruction algorithm.

It will be appreciated that Workflow C of FIG. 4 can be implemented using the imaging controller 10 with suitable programming of the electronic processor 12. As with Workflows A and B, the previous imaging session 100 is preferably a previous imaging session of the same subject as in the current imaging session 202 (i.e., same individual and same anatomic location/orientation). However, it is alternatively contemplated for the previous CT and PET images to be of another individual, although it should still be of the same anatomic location in the same orientation, and the CT and PET images of the previous session should still be mutually spatially aligned. For example, it is contemplated for the previous imaging session 100 (i.e. the previous AC-PET 118 and the previous CT image 112) to be PET/CT study atlas images retrieved from an electronic PET/CT study atlas.

In the foregoing embodiments, imaging data and/or images 110, 112, 114, 116, 118 for the previous imaging session 100 are retrieved from the PACS. The Workflow A, B, or C of respective FIGS. 2, 3, and 4 can be started manually, or using an automated approach such as that described with reference to FIG. 1 for Workflows A and B. More generally, approaches disclosed herein provide treatment protocol-level control using a treatment protocol Binary Large Object (BLOB) data structure for collecting and storing information (or pointers to information) related to a single treatment protocol (e.g. a fractionated radiation therapy protocol for an oncology patient). This approach facilitates re-use of imaging data and/or images from a previous imaging session, e.g. as in the embodiments described with reference to FIGS. 2-4, and more generally enables re-use in a current imaging session of image planning, image acquisition and reconstruction parameters, post-processing and analysis/reporting from a previous imaging session. This improves user interfacing efficiency since the radiology technician performing the current imaging session can have the imaging scanner automatically loaded with these settings from the previous imaging session (with optional user override). This also improves the clinical value of the images generated by the current imaging session since the use of settings from the previous imaging session removes instrument-specific sources of image variability so that differences (if any) observed between images of the current imaging session and images of the previous imaging session are attributable to changes in the imaging subject, rather than due to use of different imaging system settings.

Figure 5:
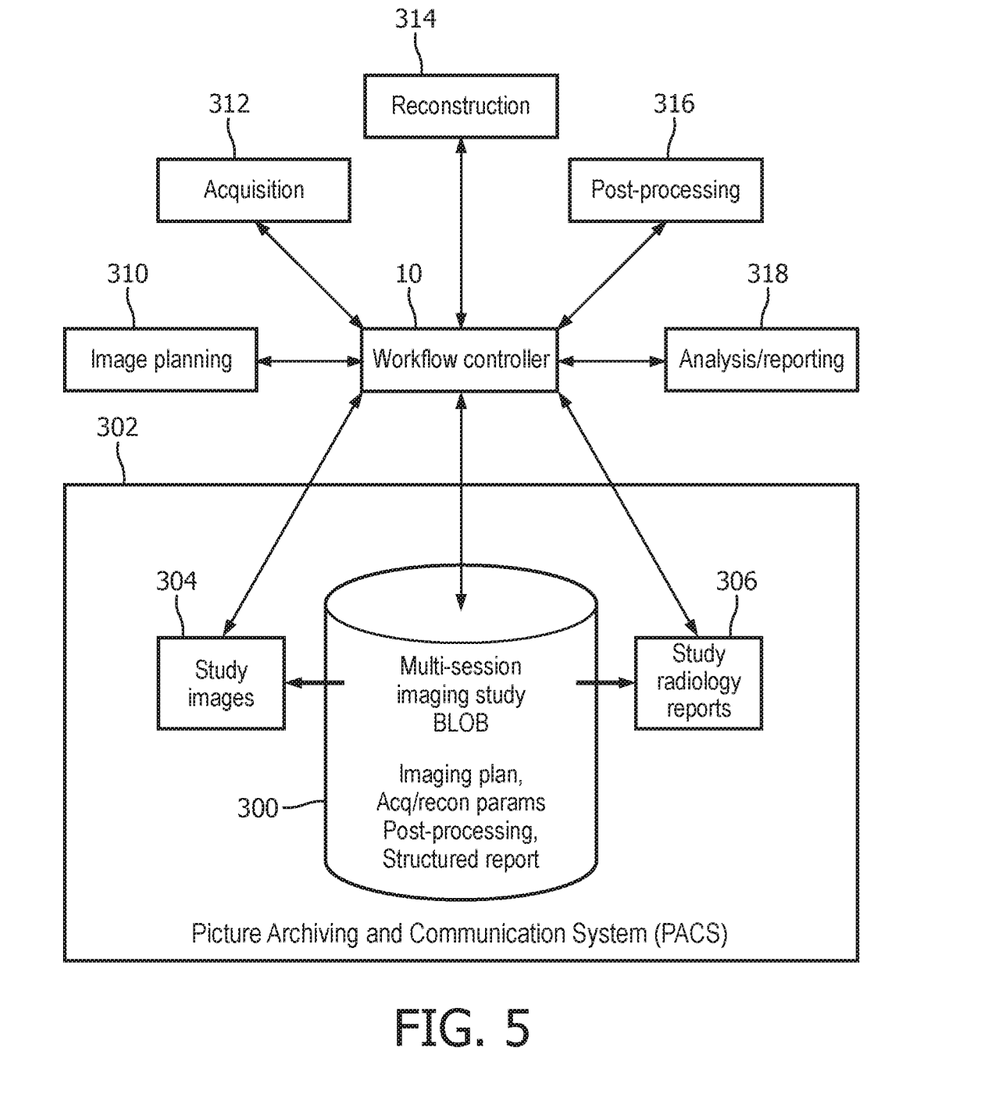
FIG. 5 diagrammatically shows an imaging system architecture enabling re-use of information from a previous imaging session of a multi-session imaging study of a subject in a current imaging session.

With reference now to FIG. 5, the workflow controller 10 of FIG. 1 is programmed to retrieve data from, and store data to, a multi-session imaging study Binary Large Object (BLOB) 300 that stores information for a multi-session imaging study of a subject including at least (in the context of the Workflows of FIGS. 2-4) the imaging data acquisition and reconstruction parameters of the previous imaging session 100. The BLOB 300 may be stored in any data storage resource with sufficient capacity to store the BLOB 300—in the illustrative example the BLOB 300 is stored in the Picture Archiving and Communication System (PACS) 302 which has the advantage of being electronically accessible by any imaging system served by the PACS 302 (typically including many or all medical imaging systems in the radiology department or hospital). Alternatively, the BLOB may be stored elsewhere, such as in the Electronic Medical or Health Record (EMR or EHR) of the patient. The BLOB 300 is suitably configured in accordance with the BLOB data type of the database system on which it is stored. Imaging study data stored in the BLOB 300 may be stored as the actual data (or copies thereof) contained in the BLOB 300, and/or may be stored as pointers to the actual data which may be located elsewhere (for example, in FIG. 5 study images 304 and study radiology reports 306 of the multi-session imaging study are stored in the PACS 302 and only pointers to these data are stored in the BLOB 300). In addition to imaging data acquisition and reconstruction parameters used in previous imaging sessions of the study, the BLOB 300 may store other information for the multi-session imaging study of the subject, such as image acquisition planning information (e.g. specifying information such as the imaged portion of the subject, subject orientation on the subject support 14, and so forth), post-processing information (e.g. identity and configuration of any post-reconstruction filters applied to the images, image segmentation results, or so forth), and data analysis and reporting such as standardized uptake value (SUV) measurements, tumor dimensions and characteristics, or so forth, e.g. stored as a structured DICOM object. In general, the BLOB 300 can be a single object, optionally having multiple sub-entities. As one example, some can be captured as "last used exam card" or "last used protocols" for individual workflow components. Some information may be stored in the BLOB 300 as pointers, e.g. to a remote system or a cloud computing resource. The BLOB 300 integrates information for the multi-session imaging study together and provides a single coherent view to the workflow engineer. The BLOB 300 may store other information of use in ensuring that the successive imaging sessions of the multi-session imaging study are comparable, such as storing an identification of the imaging device 6, 8 used in a previous imaging session, and storing the name of the radiological technician who performed the imaging session and the name of the radiologist who read the previous imaging session. The patient's weight is preferably also stored for each imaging session in the BLOB 300.

The workflow controller 10 orchestrates activities of the imaging study, using different interfaces to query the BLOB 300 in order to retrieve the information of previous workflow components. The workflow controller 10 does not need to know where the data resides as the BLOB 300 provides the interfacing by storing copies of, or pointers to, the information. Individual workflow operations such as (planning 310, acquisition 312, reconstruction 314, postprocessing 316, and analysis/reporting 318 may be implemented on a common computer or on different computers (that is, the workflow controller 10 may be embodied as a single computer or as two or more connected computers). The workflow controller 10 may be implemented as an "add-on" to an existing imaging system controller, PACS, or the like. In the following, interaction of the workflow controller 10 with individual workflow steps 310, 312, 314, 316, 318 are described as illustrative examples.

In the planning phase 310, the workflow controller 10 retrieves planning data from the BLOB 300. For example, retrieved planning data from the previous imaging session 100 may include plan lines that define the starting and ending positions of the previous scan. Those plan lines are identified on a two-dimensional survey (surview) CT image of the previous imaging session, if available. The previous surview CT image is registered to the surview CT image of the current imaging session 102, 202. As the result, the previous plan lines are mapped to the surview of the current imaging session. Those mapped plan lines are used to define the starting and ending scan positions for imaging data acquisition(s) of the current imaging session 102, 202. In another approach, a projection (coronal) image is generated from the previous volumetric CT, the projection image is registered to the surview of the current imaging session or via another 3D/2D registration technique, the first and last slice positions of the previous volumetric CT are identified on the surview of the current study, and the identified positions are used as plan lines, with some added tolerance.

It should be noted that while the findings of the previous PET/CT imaging session 100 are stored in the BLOB 300 and may be used to guide the current PET/CT imaging session 102, 202, this does not necessarily mean duplicating those previous settings. For example, the previous PET/CT imaging session 100 may have acquired a total-body scan and lesions were then found in a limited region of this total-body scan. The current imaging session 102, 202 uses this previous session information to focus on the area(s) of the lesions, so as to monitor disease progression or assess the treatment effectiveness. In one approach, the workflow controller 10 retrieves and reads the radiology report (e.g., structured DICOM report) containing the findings of the previous imaging session 102 to determine where the lesions were identified in the previous imaging session 100. The min and max z positions where the lesions were identified are calculated as: start=$\min\{z_1, \ldots, z_k\}$ and end=$\max\{z_1, \ldots, z_k\}$ where k is the number of lesions identified in the report and $z_n$ is the z position of the nth lesion. Those max and min z positions are mapped to the surview of the current imaging session 102, 202 as previously discussed (e.g. using the previous study surview or a coronal projection image). The mapped min and max z positions are used to define the plan lines, with added tolerance, and the imaging device is automatically configured with these z position minimum and maximum plan lines for the current imaging session prior to controlling the imaging system to acquire current imaging data. Instead of delineating a single scan, if the lesions are spaced apart by significant distances then radiation dosage may be further reduced by performing multiple scans. In similar fashion, the min and max plan lines may be delineated for imaging a single tumor of relatively large spatial extent, e.g. start=$z_{tumor,min}-dz_{margin}$ and end=$z_{tumor,max}+dz_{margin}$ where $z_{tumor,min}$ and $z_{tumor,max}$ are the smallest and largest z position, respectively, of the tumor, and $dz_{margin}$ is a tolerance added to ensure the plan lines accommodate any credible tumor growth that might have occurred since the previous imaging session. (It will be noted that any of these approaches which reduce the scan range for the current imaging session compared with the previous imaging session generally reduce the radiation dose delivered to the patient in the current imaging session as compared with the previous imaging session). More generally, guidance from the previous findings retrieved via the BLOB 300 enables the current imaging session to be performed in a shorter time due to reduced scan range, which speeds up the clinical workflow. The guided follow-up also reduces the CT dose exposure to the patient.

After the planning, the acquisition, reconstruction, and any post-reconstruction image processing uses parameters for the previous imaging session 100 retrieved from the BLOB 300, and the imaging controller 10 automatically configures the imaging system 6, 8 with the retrieved imaging data acquisition and reconstruction parameters of the previous imaging session 100. These parameters are preferably used as default parameters for the current imaging session 102, 202, and the radiological technician retains the ability to modify these defaults as deemed appropriate by the radiological technician (or as instructed by the physician or radiologist overseeing the multi-session imaging study).

To maximize the benefits of the automated workflow, the analysis and report from the previous imaging session 100 is used to guide the automatic analysis and report of the current imaging session 102, 202. To this end, the workflow controller 10 retrieves the findings report of the previous PET/CT imaging session 100 from the BLOB 300. The workflow controller 10 reads the report to see where the lesions were identified and how they were characterized, and registers the previous PET/CT imaging session to the current PET/CT imaging session using either 3D/3D volumetric image registration (rigid or non-rigid) or the relationship between the plan lines. In this way, the locations of the lesions from the previous PET/CT imaging session 100 are mapped to the current imaging session 102, 202. The regions of interest (ROI) or contour sets delineating the tumors are also mapped to the current imaging session space, e.g. using the spatial transform 130, 230 already described in the Workflows A, B, C of FIGS. 2-4. The workflow controller 10 searches around the mapped locations to deal with potential low registration accuracy or lesion size/shape changes between the previous and current imaging sessions. Once the lesion locations in the current imaging session space are confidently refined, the same segmentation and analysis done in the previous PET/CT imaging session 100 is performed, e.g. region growing to establish the lesion extension using the same or calibrated thresholds. If any correction method was applied, e.g. partial volume effects, it is applied in the current imaging session as well. The information on these post-processing operations is suitably stored in the BLOB 300 so as to be applied automatically. Similarly, the set of statistical measurements performed on the lesions in the previous imaging session 100 is stored in the BLOB 300 and the same set of statistical measurements is applied in the current imaging study. If the current imaging session 102, 202 identifies any new lesions that were not found in the previous imaging session 100, these can be highlighted to prompt particular review by the radiologist or physician overseeing the multi-session imaging study. A comparative report is automatically generated which compares results obtained in the current imaging session 102, 202 with results obtained in the previous imaging session 100 stored in the BLOB 300, and conclusions are drawn based on the automatic analysis. The report can include data, tables, and image captures on previous and current imaging session to support the conclusion. The report can also have hyperlinks so that the reader can access all relevant images or other supporting data to confirm and augment the automatically generated reports. The report is automatically routed to clinicians for review/update/approval.

The BLOB 300 is updated to include the current imaging session 102, 202 by storing the planning information, the imaging data acquisition and reconstruction parameters, post-reconstruction image processing parameters, and analysis/reporting information in the BLOB 300. The stored information for the current imaging session includes any changes made by automatically or by the radiological technician, such as adjustments to the min and max z positions of the plan lines, any changes made to the imaging data acquisition and/or reconstruction parameters, and includes the up-to-date findings including any changes in tumor dimensions or characteristics recorded in the structured DICOM report object. These information are stored in the BLOB 300 for use in the next imaging session (if any) of the multiple-session imaging study of the subject.

The BLOB 300 is a binary large object which provides a high degree of flexibility in storing data of various different data types, e.g. as sub-entities. It will be appreciated that some content of the BLOB 300 may be text-based content stored in the binary large object. For example, information such as the name of the radiological technician and technologist may be text information stored in the BLOB 300.

It will be appreciated that the disclosed functionality of the imaging controller 10, 12 as described with illustrative reference to FIGS. 1-5 may be embodied as a non-transitory storage medium storing instructions that are readable and executable by an electronic processor 12 to perform the disclosed functionality. The non-transitory storage medium may, for example, comprise a hard disk drive or other magnetic storage medium, an optical disk or other optical storage medium, a flash memory, read-only memory (ROM), or other electronic storage medium, various combinations thereof, or so forth.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

The invention claimed is:

1. An imaging controller comprising an electronic processor programmed to perform an imaging method executing a current imaging session which is part of a multi-session imaging study of a subject undergoing fractionated radiation therapy, the multi-session imaging study including multiple imaging sessions performed between radiation therapy sessions of the fractionated radiation therapy to assess progress of the fractionated radiation therapy, the imaging method including:

collecting and storing information for the imaging sessions of the multi-session imaging study in a Binary Large OBject (BLOB), the collected and stored information for each imaging session including at least acquisition and reconstruction parameters used in the imaging session, and tumor or lesion analysis information generated by the imaging session;

retrieving imaging data acquisition and reconstruction parameters of a previous imaging session of the multi-session imaging study from the BLOB;

automatically configuring an imaging system with the retrieved imaging data acquisition and reconstruction parameters of the previous imaging session;

after the automatic configuring, controlling the imaging system to acquire current imaging data from the subject and to reconstruct the current imaging data to generate a current image of the subject; and storing information for the current imaging session in the BLOB including at least the imaging data acquisition and reconstruction parameters used in the controlling and tumor or lesion analysis information generated from the current imaging session.

2. The imaging controller of claim 1 wherein the imaging method further includes:
retrieving spatial information for a tumor or lesion finding of the previous imaging session;
computing a reduced scan range for the current imaging session as compared with the previous imaging session using the spatial information for the tumor or lesion finding of the previous imaging session; and
prior to the controlling, automatically configuring the imaging system with the z position minimum and maximum plan lines for the current imaging session to implement the reduced scan range for the current imaging session.

3. The imaging controller of claim 1 wherein the imaging method further includes:
after the automatic configuring and before the controlling, receiving at least one change to the automatic configuration of the imaging system, wherein the controlling is performed with the retrieved imaging data acquisition and reconstruction parameters of the previous imaging session modified by the received at least one change.

4. The imaging controller of claim 1 wherein the retrieving further includes retrieving spatial parameters of at least one finding of the previous imaging session from the BLOB and the imaging method further includes:
using the retrieved spatial parameters of the at least one finding to identify a region of interest (ROI) or delineation contour in the current image.

5. The imaging controller of claim 4 wherein the imaging method further includes:
adjusting the ROI or delineation contour in the current image using a region growing or contour adjustment algorithm;
wherein the storing includes storing the adjusted ROI or delineation contour in the BLOB.

6. The imaging controller of claim 1 wherein:
the collected and stored information for each imaging session further includes identification of an imaging device used in the imaging session and identification of a radiological technician performing the imaging session; and
the storing of the information for the current imaging session hi the BLOB further includes storing identification of an imaging device used in the current imaging session and identification of a radiological technician performing the current imaging session.

7. An imaging controller comprising an electronic processor programmed to perform an imaging method executing a current imaging session which is part of a multi-session imaging study of a subject, the imaging method including:
retrieving imaging data acquisition and reconstruction parameters of a previous imaging session of the imaging study from a Binary Large OBject (BLOB) that stores information for the imaging study including at least the imaging data acquisition and reconstruction parameters of the previous imaging session;
automatically configuring an imaging system with the retrieved imaging data acquisition and reconstruction parameters of the previous imaging session;
after the automatic configuring, controlling the imaging system to acquire current imaging data from the subject and to reconstruct the current imaging data to generate a current image of the subject; and
storing the imaging data acquisition and reconstruction parameters used in the controlling in the BLOB as the imaging data acquisition and reconstruction parameters of the current imaging session of the imaging study,
wherein the current imaging data includes current emission imaging data and the imaging method further includes:
reconstructing the current emission imaging data without attenuation correction to generate a non-attenuation corrected current emission image of the subject;
retrieving a previous non-attenuation corrected emission image and a previous computed tomography (CT) image acquired in the previous imaging session from the BLOB;
generating a spatial transform to spatially align the previous non-attenuation corrected emission image to the current non-attenuation corrected emission image of the subject;
warping the previous CT image using the spatial transform to generate a warped CT image; and
reconstructing the current emission imaging data with attenuation correction performed using the warped CT image to generate an attenuation-corrected current emission image of the subject.

8. An imaging controller comprising an electronic processor programmed to perform an imaging method executing a current imaging session which is part of a multi-session imaging study of a subject, the imaging method including:
retrieving imaging data acquisition and reconstruction parameters of a previous imaging session of the imaging study from a Binary Large OBject (BLOB) that stores information for the imaging study including at least the imaging data acquisition and reconstruction parameters of the previous imaging session;
automatically configuring an imaging system with the retrieved imaging data acquisition and reconstruction parameters of the previous imaging session;
after the automatic configuring, controlling the imaging system to acquire current imaging data from the subject and to reconstruct the current imaging data to generate a current image of the subject; and
storing the imaging data acquisition and reconstruction parameters used in the controlling in the BLOB as the imaging data acquisition and reconstruction parameters of the current imaging session of the imaging study;
wherein the current imaging data includes current emission imaging data and current computed tomography (CT) imaging data of the subject and the imaging method further includes:
retrieving a previous CT image and a previous attenuation corrected emission image acquired in the previous imaging session from the BLOB;
reconstructing the current CT imaging data to generate a current CT image;
generating a spatial transform to spatially align the previous CT image to the current CT image of the subject;
warping the previous attenuation corrected emission image using the spatial transform to generate a warped attenuation corrected emission image; and
reconstructing the current emission imaging data with attenuation correction performed using the current CT image and using the warped attenuation corrected emission image as prior data to generate an attenuation-corrected current emission image of the subject.

\* \* \* \* \*